United States Patent
Swager et al.

(10) Patent No.: US 10,684,266 B2
(45) Date of Patent: Jun. 16, 2020

(54) DETECTION OF AMINES

(71) Applicant: Massachusetts Institute of Technology, Cambridge, MA (US)

(72) Inventors: Timothy M. Swager, Newton, MA (US); Sophie Liu, Cambridge, MA (US); Graham Thomas Sazama, Chestnut Hill, MA (US)

(73) Assignee: MASSACHUSETTS INSTITUTE OF TECHNOLOGY, Cambridge, MA (US)

(*) Notice: Subject to any disclaimer, the term of this patent is extended or adjusted under 35 U.S.C. 154(b) by 0 days.

(21) Appl. No.: 15/089,526

(22) Filed: Apr. 2, 2016

(65) Prior Publication Data

US 2016/0290980 A1    Oct. 6, 2016

Related U.S. Application Data

(60) Provisional application No. 62/142,435, filed on Apr. 2, 2015.

(51) Int. Cl.
  *G01N 33/12* (2006.01)
  *G01N 27/12* (2006.01)
  *G01N 33/00* (2006.01)

(52) U.S. Cl.
  CPC .......... *G01N 33/12* (2013.01); *G01N 27/127* (2013.01); *G01N 33/0054* (2013.01)

(58) Field of Classification Search
  CPC ... G01N 33/0054; G01N 33/12; G01N 37/127
  See application file for complete search history.

(56) References Cited

U.S. PATENT DOCUMENTS

| | | | |
|---|---|---|---|
| 2004/0157281 A1 | 8/2004 | Hulkower et al. | |
| 2005/0153052 A1 | 7/2005 | Williams et al. | |
| 2005/0248455 A1 | 11/2005 | Pope et al. | |
| 2008/0093226 A1* | 4/2008 | Briman ............... | G01N 27/127 205/775 |

OTHER PUBLICATIONS

Lai, Siu-Wai et al. "Electronic spectroscopy, photophysical properties, and emission quenching studies of an oxidatively robust perfluorinated platinum porphyrin." Inorganic Chemistry (2004) 43 3724-3732. (Year: 2004).*
Banerjee, Sarbajit et al. "Covalent surface chemistry of single-walled carbon nanotubes." Advanced Materials (2005) 17 17-29. (Year: 2005).*
Zhang, Ting et al. "Electrochemically functionalized single-walled carbon nanotube gas sensor." Electroanalysis (2006) 18 1153-1158. (Year: 2006).*
International Search Report dated Jun. 17, 2016, issued in International Application No. PCT/US2016/025790.
Written Opinion of the International Searching Authority dated Jun. 17, 2016, issued in International Application No. PCT/US2016/025790.

(Continued)

*Primary Examiner* — Christopher Adam Hixson
(74) *Attorney, Agent, or Firm* — Steptoe & Johnson LLP

(57) ABSTRACT

A sensor can include a conductive region in electrical communication with at least two electrodes, the conductive region can include a complex, and the complex can include a carbon nanotube that is functionalized by a porphyrin.

14 Claims, 17 Drawing Sheets

(56) References Cited

OTHER PUBLICATIONS

Mahendra D. Shirsat et al: "Porphyrin-Functionalized Single-Walled Carbon Nanotube Chemiresistive Sendor Arrays for VOCs", Journal of Physical Chemistry C, vol. 116, No. 5, Feb. 9, 2012 (Feb. 9, 2012), pp. 3845-3850, XP055277297, US ISSN: 1932-7447, DOI: 10.1021/jp210582t abstract p. 3846, col. 1, paragraph 1—p. 3848, col. 1, paragraph 1: figure 4.

Neal A. Rakow el al.: "Molecular Recognition and Discrimination of Amines with a Colorimetric Array", Angewandte Chemie International Edition, vol. 44, No. 29, Jul. 18, 2008 (Jul. 18, 2005), pp. 4528-4532, XP055277408, DE ISSN: 1433-7851, DOI: 10.1002/anie.200500939 p. 4529, col. 1, paragraph 1—p. 4531, col. 2, paragraph 3; figures 1, 2, 5 & Neal A. Rakow: "Supporting Information", Jul. 18, 2005 (Jul. 18, 2005), XP055277407.

Swati Saxena et al: "Metal-tetraphenylporphyrin functionalized carbon nanotube composites as sensor for benzene, tolune and xylene vapors", Adv. Mat. Lett, vol. 5, No. 8, Aug. 31, 2014 (Aug. 31, 2014), pp. 472-478, XP055277382, DOI: 10.5185/amlett.2013.2429 abstract p. 473, col. 1, paragraph 2—p. 477, col. 2, paragraph 2: figures 1, 3-4, 7-8; table 1.

Di Natale C. et al: "An electronic nose for food analysis", Sensors and Actuators B, vol. 44, No. 1-3, Oct. 1, 1997 (Oct. 1, 1997), pp. 521-526, XP004117141, ISSN: 0925-4005, DOI: 10.1016/S0925-4005 (97)00175-5 p. 552, column 1, paragraph 2—p. 524, col. 1, paragraph 3; figures 1-2.

Hiroshi Sugimoto et al: "Preparation and physicochemical properties of tervalent cobalt complexes of porphyrins.", Bulletin of the Chemical Society of Japan, vol. 54, No. 11, Jan. 1, 1981 (Jan. 1, 1981), pp. 3425-3432, XP055277397, JP ISSN: 0009-2673, DOI: 10.1246/bcsj.54.3425 abstract p. 3425, col. 2, paragraph 1.

Penza M. et al: "Metalloporphyrins-modified carbon nanotubes networked films-based chemical sensors for enhanced gas sensitivity", Sensors and Actuators B, vol. 144, No. 5, Feb. 17, 2010 (Feb. 17, 2010), pp. 387-394, XP026888317, ISSN: 0925-4005, DOI: 10.1016/J.SNB.2008.12.060 [retrieved on Jan. 6, 2009] abstract p. 387, col. 2, paragraph 4—p. 392, col. 1, paragraph 1; figures 3, 4, 8, 10, 11.

Sophie F. Liu et al: "Single-Walled Carbon Nanotube/Metalloporphyrin Composites for Chemiresistive Detection of Amines and Meat Spoilage", Angewandte Chemie International Edition, vol. 54, No. 22, Apr. 13, 2015 (Apr. 13, 2015), pp. 6554-6557, XP055218982, DE ISSN: 1433-7851, DOI: 10.1002/anit.201501434 p. 6554, col. 1, paragraph 1—p. 6556, col. 2, paragraph 3: figures 1-6.

* cited by examiner

DETECTION OF AMINES

CLAIM OF PRIORITY

This application claims the benefit of prior U.S. Provisional Application No. 62/142,435 filed on Apr. 2, 2015, which is incorporated by reference in its entirety.

FEDERAL SPONSORSHIP

This invention was made with government support under Grant No. DMR-1410718 awarded by the National Science Foundation and under Contract No. W911NF-13-D-0001 awarded by the Army Research Office. The government has certain rights in the invention.

TECHNICAL FIELD

The invention features a detector of amines.

BACKGROUND

A detector for meat spoilage can prevent the consumption of unsafe meat or unnecessary discard. One marker of meat decomposition is formation of biogenic amines. Methods for monitoring meat spoilage, such as chromatography, spectrometry, electrophoresis, colorimetry, mass balance, chemiluminescence, and electrochemistry, suffer from one or more drawbacks.

SUMMARY

In one embodiment, a sensor can include a conductive region in electrical communication with at least two electrodes, the conductive region including a complex, wherein the complex can include a carbon nanotube that is functionalized by a porphyrin.

In certain embodiments, the porphyrin can include a cobalt porphyrin. The cobalt porphyrin can include a $Co^{3+}$. The cobalt porphyrin can include a $Co^{2+}$.

In certain embodiments, the carbon nanotube can be non-covalently functionalized by the porphyrin. In certain embodiments, the carbon nanotube can be covalently functionalized by a porphyrin. These covalent functionalization can be accomplished through a diversity of reactions to create new chemical bonds between the porphyrin and the carbon nanotube and include but are not limited to 1,3-dipolar cycloadditions, reaction with a diazonium ion, coupling reactions to produce an amide linkage, nucleophilic substitution reactions, carbene additions, and nitrene additions.

In certain embodiments, the complex can include a cobalt meso-arylporphyrin complex. In certain embodiments, the complex can include a meso-tetrakis(pentafluorophenyl) porphyrinato.

In certain embodiments, the complex can include a meso-tetraphenylporphyrinato. In certain embodiments, the complex can include a meso-arylporphyrin.

In certain embodiments, the porphyrin can include a $ClO_4^-$. In certain embodiments, the porphyrin can include a $BF_4^-$. In certain embodiments, the porphyrin can include a $Cl^-$. In certain embodiments, the carbon nanotube can be a single-walled carbon nanotube.

In another embodiment, a method of sensing an analyte can include exposing a sensor to a sample and measuring an electrical property at the electrodes. The sensor can include a conductive region in electrical communication with at least two electrodes, the conductive region including a complex, wherein the complex includes a carbon nanotube that is functionalized by a porphyrin.

In certain embodiment, the method can include detecting an amine. In certain embodiment, the method can include detecting a putrescine. In certain embodiment, the method can include detecting a cadaverine.

In certain embodiment, the detection can be semi-reversible. In certain embodiment, the method can include detecting the analyte below 0.5 ppm. In certain embodiment, the method can include detecting the analyte below 1 ppm. In certain embodiment, the method can include detecting the analyte wirelessly.

In certain embodiment, the method can include detecting the analyte through a wireless radio frequency communication. In certain embodiment, the method can include detecting an output from a radio frequency identification tag including the sensor. In certain embodiment, the method can include detecting nitrogen content.

In certain embodiment, the method can include non-covalently functionalizing the carbon nanotube. In certain embodiment, the method can include covalently functionalizing the carbon nanotube.

In another embodiment, a method of preparing a sensor can include forming a complex including a conductive region in electrical communication with at least two electrodes, the conductive region including a complex, wherein the complex includes a carbon nanotube that is functionalized by a porphyrin; and placing the conductive material in electrical communication with at least two electrodes.

In another embodiment, a food packaging can include a sensor, wherein the sensor can include a conductive region in electrical communication with at least two electrodes, the conductive region including a complex, wherein the complex can include a carbon nanotube that is functionalized by a porphyrin.

Other aspects, embodiments, and features will be apparent from the following description, the drawings, and the claims.

DETAILED DESCRIPTION

Figure 1:
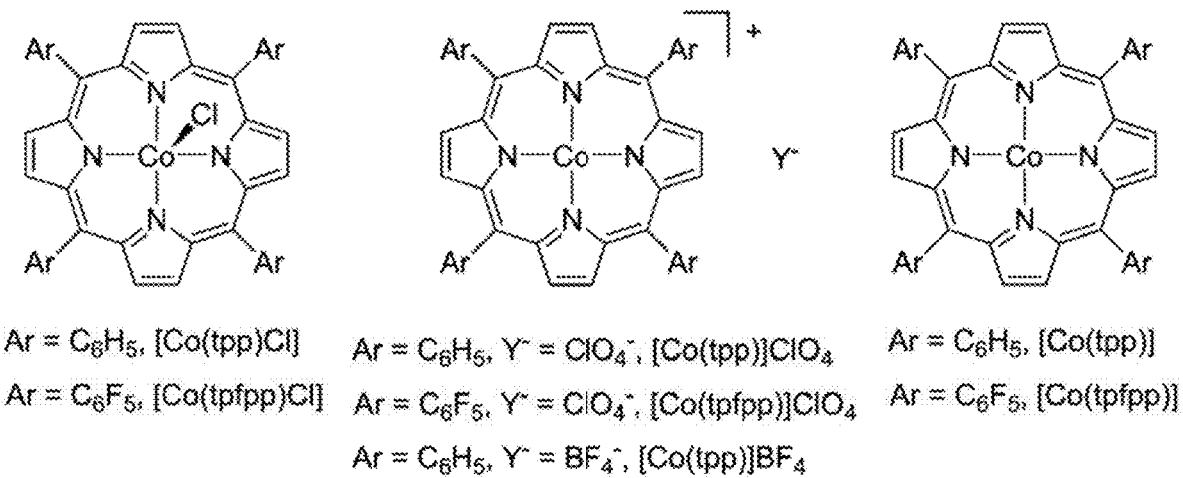
FIG. 1 shows structures of cobalt porphyrins employed in detectors. Axial aquo ligands are omitted for clarity.

Chemiresistive detectors for amine vapors can be made from carbon nanotubes by non-covalent modification with cobalt meso-arylporphyrin complexes. Carbon nanotubes (CNTs) are allotropes of carbon with a cylindrical nanostructure.

Carbon Nanotubes

Carbon nanotubes can be constructed with length-to-diameter ratio of up to 132,000,000:1, significantly larger than for any other material. These cylindrical carbon molecules have unusual properties, which are valuable for nanotechnology, electronics, optics and other fields of materials science and technology. In particular, owing to their extraordinary thermal conductivity and mechanical and electrical properties, carbon nanotubes find applications as additives to various structural materials.

Carbon nanotubes are members of the fullerene structural family. These sheets are rolled at specific and discrete (chiral) angles, and the combination of the rolling angle and radius decides the nanotube properties. For example, whether the individual nanotube shell is a metal or semiconductor. Nanotubes are categorized as single-walled nanotubes (SWNTs) and multi-walled nanotubes (MWNTs). Individual nanotubes naturally align themselves into "ropes" held together by van der Waals forces, more specifically, pi-stacking.

Applied quantum chemistry, specifically, orbital hybridization best describes chemical bonding in nanotubes. The chemical bonding of nanotubes is composed entirely of sp2 bonds, similar to those of graphite. These bonds, which are stronger than the sp3 bonds found in alkanes and diamond, provide nanotubes with their unique strength.

Porphyrin

Porphyrins are a group of heterocyclic macrocycle organic compounds, composed of four modified pyrrole subunits interconnected at their a carbon atoms via methine bridges (=CH—). The parent porphyrin is porphin, and substituted porphines are called porphyrins. The porphyrin ring structure is aromatic, with a total of 26 electrons in the conjugated system. Various analyses indicate that not all atoms of the ring are involved equally in the conjugation or that the molecule's overall nature is substantially based on several smaller conjugated systems.

Porphyrins are the conjugate acids of ligands that bind metals to form complexes. The metal ion usually has a charge of 2+ or 3+. A schematic equation for these syntheses is shown:

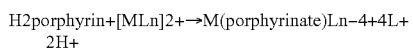

where M=metal ion and L=a ligand

A porphyrin without a metal-ion in its cavity is a free base.

Several other heterocycles are related to porphyrins. These include corrins, chlorins, bacteriochlorophylls, and corphins. Chlorins (2,3-dihydroporphyrin) are more reduced, contain more hydrogen than porphyrins, and feature a pyrroline subunit. This structure occurs in a chlorophyll molecule. Replacement of two of the four pyrrolic subunits with pyrrolinic subunits results in either a bacteriochlorin (as found in some photosynthetic bacteria) or an isobacteriochlorin, depending on the relative positions of the reduced rings. Some porphyrin derivatives follow Hilckel's rule, but most do not.

A benzoporphyrin is a porphyrin with a benzene ring fused to one of the pyrrole units. eg verteporfin is a benzoporphyrin derivative.

Researchers have reported porphyrin-functionalized CNTs bound covalently with an ester linkage, in which CNTs bearing carboxylic groups on the sidewall and at the terminal were esterified with hydroxyl porphyrins. See, e.g., Baskaran D, Mays J W, Zhang X P, Bratcher M S. J. 2005. p. 6916, incorporated by reference herein.

Researchers have also reported the synthesis of a novel covalently porphyrin-functionalized single walled carbon nanotube nanohybrid constructed with a unique direct linkage using in situ generated diazonium compounds. See, e.g., Guo Z, Du F, Ren D M, Chen Y S, Zheng J Y, Liu Z B, Tian J G. J. 2006. p. 3021, incorporated by reference herein.

Generally, there are two disadvantages in porphyrin-functionalized CNTs process, one is the low quantity porphyrin (<20 wt %) grafted to the surface of CNTs, another is that the structure of CNTs was badly destroyed because carboxyl groups on MWNT surface are prepared by strong oxidative acid treatment. There have been few reports on the functionalization of CNTs to overcome these two weaknesses simultaneously. However, when a covalent porphyrin and its complexes (Co2+, Zn2+) functionalized by MWNTs, they were successfully synthesized by the reaction of the carboxyl on the surface of MWNTs which was synthesized to use carbon radicals generated by the thermal decomposition of azodiisobutyronitrile (AIBN) with 5-p-hydroxy-phenyl-10,15,20-triphenyl-porphyrin and its complexes (Co2+, Zn2+). The quality of porphyrin attached to the MWNTs was determined from thermogravimetric analysis (TGA) of the MWNTs, which showed a weight loss of about 60%.

Carbon nanotube (CNT) compositions can be prepared by covalently grafting a Co(II) porphyrin to functionalized multiwalled carbon nanotubes (MWCNTs) via zwitterionic functionalization of the CNT sidewalls followed by a SN2 substitution reaction. The MWCNT-Co-porphyrin compositions, mixed with Nafion, displayed excellent catalytic performance for oxygen reduction in acidic media (pH range, 0.0-5.0) at room temperature. With low catalyst loading, the oxygen reduction rates achieved are more than 1 order of magnitude higher than previously reported values for similar Co-porphyrin catalysts. These results demonstrate the advantages of systems of MWCNTs covalently linked to electrocatalytic molecules. The electrodes are easily fabricated by a drop-casting vacuum drying procedure. Rotating disk electrode (RDE) and rotating ring disk electrode (RRDE) measurements revealed the mechanism to be a direct four-proton and four-electron reduction of oxygen to water. These results demonstrate that new MWCNT electrocatalytic systems are potential substitutes for platinum or other metal-based cathode materials in proton conducting membrane fuel cells. This is described, for example in Cobalt Porphyrin Functionalized Carbon Nanotubes for Oxygen Reduction, *Chem. Mater,* 2009, 21(14), pp. 3234-3241 (June 2009), incorporated by reference herein.

Used to Detect Spoilage

Putrescine, or tetramethylenediamine, is a foul-smelling organic chemical compound NH2(CH2)4NH2 (1,4-diaminobutane or butanediamine) that is related to cadaverine; both are produced by the breakdown of amino acids in living and dead organisms and both are toxic in large doses.

Cadaverine is a foul-smelling diamine compound produced by protein hydrolysis during putrefaction of animal tissue. Cadaverine is a toxic diamine with the formula $NH_2(CH_2)_5NH_2$, which is similar to putrescine. Cadaverine is also known by the names 1,5-pentanediamine and pentamethylenediamine.

Through changes in the metal's oxidation state, the electron-withdrawing character of the porphyrinato ligand, and the counteranion, the magnitude of chemiresistive response to ammonia can be improved. The devices can exhibit sub-ppm sensitivity and high selectivity toward amines as well as good stability to air, moisture, and time. These chemiresistors can be used in the detection of various biogenic amines (e.g., putrescine, cadaverine) and in the monitoring of spoilage in raw meat samples (e.g., chicken, pork, salmon, cod).

Sensor Properties and Applications

Interest in the synthesis and study of porphyrin complexes with variable valence metals results from their potential application as chemical sensors, photo chromic materials, and redox catalysts.

A sensor can include a conductive region in electrical communication with at least two electrodes, the conductive region including a complex, and the complex includes a carbon nanotube that is functionalized by a porphyrin. The functionalization can be covalent or non-covalent. The carbon nanotube can be covalently functionalized by a porphyrin by a bond between a phenyl group pendant to the porphyrin and the carbon nanotube though 1,3-dipolar cycloadditions, reaction with a diazonium ion, coupling reactions to produce an amide linkage, nucleophilic substitution reactions, carbene additions, and nitrene additions. Other types of functionalization can also be used. See, for example, Guo, Z.; Du, F.; Ren, D.; Chen, Y.; Zheng, J.; Liu, Z.; Tian, J. J. Mater. Chem. 2006, 16, 3021; Lipinska, M. E.; Rebelo, S. L. H.; Pereira, M. F. R.; Figueiredo, J. L.; Freire, C. Mater. Chem. Phys. 2013, 143, 296-304; Zhang, W.; Shaikh, A. U.; Tsui, E. Y.; Swager, T. M. Chem. Mater. 2009, 21, 3234-3241, each of which is incorporated by reference in its entirety. The sensor can behave as a dosimeter giving an irreversible response to one or more nitrogen bases.

For health and economic reasons, there is interest from meat providers and consumers in sensors to monitor its spoilage. See, for example, K.-H. Eom, et al., Int. J. Distrib. Sens. Networks 2014, 2014, 1-9, which is incorporated by reference in its entirety. A detector for meat spoilage can prevent the consumption of unsafe meat or unnecessary discard. One marker of meat decomposition is formation of biogenic amines (BAs). Among the BAs in food are putrescine (butane-1,4-diamine) and cadaverine (pentane-1, 5-diamine). BAs are formed through microbial enzymatic decarboxylation of amino acids and by amination of carbonyls. See, for example, A. Naila, et al., J. Food Sci. 2010, 75, R139-R150; J. Karovičová, et al., Chem. Pap. 2005, 59, 70-79, each of which is incorporated by reference in its entirety.

Many methods for monitoring meat spoilage rely on detection of amines, or total volatile basic nitrogen (TVBN). Strategies for the detection of BAs include chromatography, spectrometry, electrophoresis, colorimetry, mass balance, chemiluminescence, and electrochemistry. See, for example, Z. Karpas, et al., Anal. Chim. Acta 2002, 463, 155-163; L. V. Jorgensen, et al., J. Agric. Food Chem. 2001, 49, 2376-2381; A. Kovacs, et al., J. Chromatogr. A 1999, 836, 305-313; H. Li, et al., Anal. Methods 2014, 6, 6271-6277; b) T. L. Nelson, et al., Analyst 2007, 132, 1024-1030; c) M. S. Maynor, et al., Org. Lett. 2007, 9, 3217-3220; C. Di Natale, et al., Sens. Actuators, B 1997, 44, 521-526; Y. Yano, et al., Lebensm.-Wiss. u.-Technol. 1996, 29, 498-502; M. Wimmerová, et al., Biosens. Bioelectron. 1999, 14, 695-702; D. Carelli, et al., Biosens. Bioelectron. 2007, 23, 640-647, each of which is incorporated by reference in its entirety. However, these all suffer from one or more drawbacks: extensive sample preparation prior to analysis; expensive, cumbersome instruments with high power consumption; highly trained personnel to operate; and line of sight required to read output.

Electronic sensors such as chemiresistors offer solutions to these drawbacks. They can take measurements in real time with the as-is sample; they can be fabricated cheaply; they can be portable with low power requirements and readily integrated into electronic circuitry without direct visual (line of sight) observation needed to obtain the readout. Carbon nanotubes are particularly well suited for use in chemiresistors as they are highly sensitive to changes in their electronic environments and do not require high operating temperatures. See, for example, U. Latif, et al., Sensors 2011, 11, 8611-8625; D. R. Kauffman, et al., Angew. Chem. 2008, 120, 6652-6673; b) D. R. Kauffman, et al., Angew. Chem. Int. Ed. 2008, 47, 6550-6570; P. M. Schweizer-Berberich, et al., Sens. Actuators, B 1994, 19, 282-290, each of which is incorporated by reference in its entirety.

Although non-functionalized single-walled carbon nanotubes (SWCNTs) can detect amines chemiresistively, their sensitivity and specificity to amines can be improved through functionalization.

Functionalization of CNTs

SWCNTs can be functionalized covalently or non-covalently with other molecules in order to impart sensitivity or selectivity for a desired analyte. See, for example, K. A. Mirica, et al., Angew. Chem. 2012, 124, 10898-10903; K. A. Mirica, et al., Angew. Chem. Int. Ed. 2012, 51, 10740-10745; J. M. Schnorr, et al., Chem. Mater. 2011, 23, 646-

657, each of which is incorporated by reference in its entirety. In particular, non-covalent functionalization allows for facile functionalization without disruption of the electronic properties of the CNTs that can accompany covalent functionalization. See, for example, W. Maser, et al., in Functionalized Nanoscale Materials, Devices and Systems (Eds.: A. Vaseashta, I. N. Mihailescu), Springer, Dordrecht, The Netherlands, 2008, pp. 101-120, which is incorporated by reference in its entirety.

Covalent functionalization is based on the formation of a covalent linkage between functional entities and the carbon skeleton of nanotubes. It could also be divided into direct covalent sidewall functionalization and indirect covalent functionalization with carboxylic groups on the surface of CNTs. Direct covalent sidewall functionalization is associated with a change in hybridization from sp2 to sp3 and a simultaneous loss of conjugation. Indirect covalent functionalization takes advantage of chemical transformations of carboxylic groups at the open ends and holes in the sidewalls. These carboxylic groups might have existed on the as-grown CNTs and also be further generated during oxidative purification. In order to increase the reactivity of CNTs, the carboxylic acid groups usually need to be converted into acid chloride and then undergo an esterification or amidation reaction. The drawback of covalent functionalization is that the perfect structure of CNTs has to be destroyed, resulting in significant changes in their physical properties.

Non-covalent functionalization is mainly based on supramolecular complexation using various adsorption forces, such as Van der Waals force, hydrogen bonds, electrostatic force and π-stacking interactions. Compared to the chemical functionalization, non-covalent functionalization has the advantages that it could be operated under relatively mild reaction conditions and the perfect graphitic structure of CNTs could be maintained.

Porphyrins are an attractive platform for functionalizing SWCNTs because their aromatic core is capable of non-covalently binding to the walls of the SWCNTs with the π system. See, for example, A. Satake, et al., *Chem. Mater.* 2005, 716-724; H. Murakami, et al., *Chem. Phys. Lett.* 2003, 378, 481-485; Q. Zhong, et al., *ACS Nano* 2013, 7, 3466-3475; H. Li, et al., *J. Am. Chem. Soc.* 2004, 126, 1014-1015, which is incorporated by reference in its entirety.

To detect amines, SWCNTs can be functionalized with cobalt porphyrins, which can bind to amines, can be tuned rationally, and offer an opportunity to examine the effects of oxidation state in amine sensing as both $Co^{2+}$ and $Co^{3+}$ species are accessible. See, for example, H. Sugimoto, et al., *Bull. Chem. Soc. Jpn.* 1981, 54, 3425-3432, which is incorporated by reference in its entirety. The synthesis and properties of cobalt(II) and cobalt(III) are described, for example, by Chizhova, N. V., et al., Synthesis and Spectral Properties of Cobalt (II) and Cobalt (III) Tetraarylporphyrinates, *Russian J. of Inorganic Chemistry*, Vol. 58, No. 6, 2013, pp. 836-840, also incorporated by reference herein.

The sensitivity to amines can benefit from increasing electrophilicity of the Co center by using a relatively electron-withdrawing porphyrin, a weakly coordinating counteranion, and a high oxidation state. A series of Co porphyrins (FIG. 1) can be synthesized for comparison between meso-tetraphenylporphyrinato (tpp) and the more electron-withdrawing meso-tetrakis(pentafluorophenyl)porphyrinato (tpfpp) ligand, between $Cl^-$ and the more weakly coordinating $ClO_4^-$ and $BF_4^-$ counteranions, and between $Co^{3+}$ and more electron-rich $Co^{2+}$.

Cobalt(III) porphyrins incorporated in a SWNT network can be active in the chemoresistive detection of an analyte. Sensitivity to an analyte can benefit from increasing the electrophilicity of the cobalt(III) center toward amines through the use of both a relatively electron-withdrawing porphyrin ligand and a weakly coordinating counter anion. Therefore, a series of cobalt(III) porphyrins can allow for comparison between 5,10,15,20-tetraphenylporphyrinato (tpp) and the more electron-withdrawing 5,10,15,20 tetrakis (pentafluorophenyl)porphyrinato (tpfpp) ligand as well as between $Cl^-$ and the more weakly coordinating $ClO_4^-$ counteranion.

Porphyrins with a sterically protected metal center may provide enhanced selectivity by excluding compounds that are larger or that would bind to the metal center in an $\eta_1$ fashion perpendicular to the approximate plane of the porphyrin ring (e.g., CO, MeCN). A canopied pyrrole can give such protection by restricting the space around a tervalent group 9 metal center when incorporated into a porphyrin ligand's structure, preventing the binding of larger interferent molecules and other coordinating volatile organic compounds while still allowing the particularly small molecule to access the metal center in a flatter, side-on fashion and potentially excluding larger molecules that can be forced to bind end-on due to the canopy's obstruction of space higher above the metal center.

A chemiresistive detector for amines can be fabricated from Co porphyrin/SWCNT composites. Tuning the Co oxidation state, ligand, and primary coordination sphere of the complex can lead to improvements in sensitivity toward amines, which are detected rapidly at sub-ppm concentrations and with high selectivity. The devices can be used to monitor meat for spoilage by detecting volatile BAs. The system represents an inexpensive, portable method for following the decomposition of various types of meat.

EXAMPLE

The (6,5) chirality-enriched SWNTs (SG65) were purchased from SouthWest NanoTechnologies. Carbon monoxide gas (99.3%) was purchased from Airgas. 5,10,15,20-Tetrakis(pentafluorophenyl)porphyrin ($tpfppH_2$) was purchased from Frontier Scientific. Perchloric acid (70%) was purchased from Sigma-Aldrich. Aluminum oxide (activated, neutral, Brockmann Grade I, 58 Å) was purchased from Alfa Aesar. Solvents were purchased from Sigma-Aldrich or Avantor Performance Materials (Macron Fine Chemicals or J. T. Baker) and used as received.

UV-Vis spectra were recorded on a Cary 4000 UV-visible spectrophotometer. FT-IR spectroscopy was performed with use of a Thermo Scientific Nicolet 6700 FT-IR spectrometer (ATR mode, Ge). NMR spectra were recorded using a Bruker Avance 400 MHz NMR spectrometer and were referenced to the proton resonances resulting from incomplete deuteration of the NMR solvent ($^1H$) or to α,α,α-trifluorotoluene added as an internal reference standard ($^{19}F$).

Cyclic voltammetric measurements were taken using a Biologic VMP3 potentiostat with a scan rate of 100 mV/s under $N_2$ gas using a Ag/Ag+ pseudo-reference electrode, Pt counter electrode, and glassy carbon working electrode in benzonitrile solvent with 0.1 M tetra-n-butylammonium hexafluorophosphate supporting electrolyte. Potentials were referenced to $Fc/Fc^-$.

Synthetic Procedures 5,10,15,20-Tetraphenylporphyrin ($tppH_2$), 5,10,15,20-tetraphenylporphyrinatocobalt(II) [Co(tpp)], 5,10,15,20-tetrakis(pentafluorophenyl)porphyrinatocobalt(II) [Co(tpfpp)], chloro(5,10,15,20-tetraphenylporphyrinato)cobalt(III) monohydrate [Co(tpp)Cl(H$_2$O)], 5,10,15,20-tetraphenylporphyrinatocobalt(III) perchlorate dihydrate [Co(tpp)(H$_2$O)$_2$]ClO$_4$, and 5,10,15,20-tetraphenylporphyrinatocobalt(III) tetrafluoroborate dihydrate [Co(tpp)(H$_2$O)$_2$]BF$_4$ were synthesized according to literature procedures. See, for example, Adler, A. D., et al., J. Org. Chem. 1966, 32, 476; Dorough, G. D., et al., J. Am. Chem. Soc. 1951, 73, 4315-4320; Kadish, K. M., et al., J. Am. Chem. Soc. 1990, 112, 8364-8368; Sakurai, T., et al., Bull. Chem. Soc. Jpn 1976, 49, 3042-3046; Sugimoto, H., et al., Bull. Chem. Soc. Jpn 1981, 54, 3425-3432, which is incorporated by reference in its entirety.

Synthesis of 5,10,15,20-tetrakis(pentafluorophenyl)porphyrinatocobalt(III) perchlorate dihydrate, [Co(tpffip)(H$_2$O)$_2$]ClO$_4$

[Co(tpfpp)] (0.060 g, 0.058 mmol) was dissolved in methanol (60 mL). A 10% aqueous HClO$_4$ solution (2 mL) was added, and air was bubbled through the solution while stirring for 72 h at rt. The reaction mixture was concentrated with use of rotary evaporation. The resulting purple crystals were isolated by vacuum filtration and allowed to dry under air to give the product (0.043 g) in 66% yield. $^1$H NMR (400 MHz, CD$_3$OD): δ 9.65 (s); $^{19}$F NMR (376 MHz, CD$_3$OD): δ −140.24 (dd, 8F, J=21 and 6.8 Hz), −154.26 (t, 4F, J=21 Hz), −164.14 (td, 8F, J=21 and 6.8 Hz).

Synthesis of chloro(5,10,15,20-tetrakis(pentafluorophenyl)porphyrinato)cobalt(III) monohydrate, [Co(tpfpp)Cl(H$_2$O)]

[Co(tpfpp)] (0.060 g, 0.058 mmol) was dissolved in methanol (60 mL). Concentrated HCl (0.6 mL) was added, and air was bubbled through the solution while stirring for 72 h at rt. The reaction mixture was concentrated with use of rotary evaporation. The resulting purple crystals were isolated by vacuum filtration and allowed to dry under air to give the product (0.023 g) in 37% yield. $^1$H NMR (400 MHz, CD$_3$OD): δ 9.65 (s); $^{19}$F NMR (376 MHz, CD$_3$OD): δ −140.23 (dd, 8F, J=21 and 6.8 Hz), −154.24 (t, 4F, J=21 Hz), −164.12 (td, 8F, J=21 and 6.8 Hz).

Device Preparation

Devices were prepared on microscope glass slides (VWR) cleaned by sonication in acetone. The glass slides were fitted with a custom aluminum mask, and using a thermal evaporator purchased from Angstrom Engineering, a 10 nm layer of chromium (99.99%, R. D. Mathis) was deposited onto the glass, followed by 100 nm of gold (99.99%, R. D. Mathis).

In a typical device, 0.25 mg (21 μmol C) of SWNTs and 0.44 mmol porphyrin were suspended in 1.0 mL 1,2-dichlorobenzene and sonicated briefly at room temperature. The resulting dispersion was drop-casted using a micropipette onto the glass slide in between the gold electrodes. The solvent was removed in vacuo. The application of the dispersion followed by the removal of the solvent was repeated until the resistance across the SWNT network reached a resistance of 10-100 kΩ as measured by a multimeter.

Crystallographic Details

Low-temperature diffraction data of [(tpfpp)Co(ClO4)] (φ- and ω-scans) were collected on a Bruker-AXS X8 Kappa Duo diffractometer coupled to a Smart APEX2 CCD detector with an micro-source Mo Kα radiation (λ=0.71073 Å). Absorption and other corrections were applied using SADABS. All structures were solved by direct methods using SHELXS, and refined against F2 on all data by full-matrix least squares with SHELXL-97. See, for example, G. M. Sheldrick, Acta Cryst. 2008, A64, 112-122, which is incorporated by reference in its entirety. A summary of crystal and refinement data is shown in table 1.

The complex [(tpfpp)Co(ClO$_4$)] crystallized in the P¯1 space group with one molecule of [(tpfpp)Co]$^+$ and one each of a non-coordinating perchlorate anion and benzene molecule. Additional disordered methanol and water solvents occupied coordination sites and free space on the faces of the cobalt complex proximal and distal to the perchlorate anion. On the side of the complex proximal to the perchlorate, a hydrogen-bonded chain of three methanol molecules terminates in a hydrogen bond to a perchlorate oxygen atom. The cobalt-bound methanol shows positional disorder of the methyl groups. The distal side of the molecule was modeled as a three part disorder, using the SUMP command to ensure chemically reasonable disorder models and hydrogen bonding networks. The cobalt has either a water molecule or one of two positionally disordered methanol molecules bound. These are hydrogen bonded to a methanol on either side, as appropriate based on the O¬H position. One of the hydrogen bonded methanols is also positionally disordered.

All hydrogen atoms were included into the model at geometrically calculated positions and refined using a riding model, unless otherwise noted. The isotropic displacement parameters of all hydrogen atoms were fixed to 1.2 times the Ueq value of the atoms they are linked to (1.5 times for methyl groups). The distance of all oxygen-bound methanol and water hydrogen atoms was fixed to 0.84 Å using distance restraints, and similarity restraints were placed on the carbon-hydrogen and cobalt-hydrogen distances for methanol, and the hydrogen-hydrogen distance for water was restrained to 1.33 Å. Carbon-cobalt 1,3 distances were also restrained with similarity restraints for the proximal Co-bound methanols. Finally, similar ADP restraints were employed for the distal side solvent molecules, as well as isotropic approximation restraints for the cobalt-bound distal methanols. The two proximal methanol carbons, c1b and c1c, required the ADPs to be constrained as equal.

Table 1 shows crystal data and structure refinement for SL001. Table 2 shows atomic coordinates and equivalent isotropic displacement parameters for SL001.

TABLE 1

Crystal data and structure refinement for SL001.

| | |
|---|---|
| Identification code | SL001 |
| Empirical formula | C55 H35 Cl Co F20 N4 O9.49 |
| Formula weight | 1378.21 |
| Temperature | 100(2) K |
| Wavelength | 0.71073 Å |
| Crystal system | Triclinic |
| Space group | P-1 |
| Unit cell dimensions | a = 14.5161(16) Å    α = 60.248(2)°. |
| | b = 15.2922(19) Å    β = 74.322(3)°. |
| | c = 15.3546(19) Å    γ = 71.146(2)°. |
| Volume | 2775.2(6) Å$^3$ |
| Z | 2 |
| Density (calculated) | 1.649 Mg/m$^3$ |
| Absorption coefficient | 0.487 mm$^{-1}$ |
| F(000) | 1386 |
| Crystal size | 0.30 × 0.25 × 0.15 mm$^3$ |
| Theta range for data collection | 1.50 to 31.56°. |
| Index ranges | −21 <= h <= 21, −22 <= k <= 22, −21 <= l <= 22 |
| Reflections collected | 201135 |
| Independent reflections | 18373 [R(int) = 0.0282] |

TABLE 1-continued

Crystal data and structure refinement for SL001.

| | |
|---|---|
| Completeness to theta = 31.56° | 98.9% |
| Absorption correction | Semi-empirical from equivalents |
| Max. and min. transmission | 0.9305 and 0.8676 |
| Refinement method | Full-matrix least-squares on $F^2$ |
| Data/restraints/parameters | 18373/182/899 |
| Goodness-of-fit on $F^2$ | 1.029 |
| Final R indices [I > 2sigma(I)] | R1 = 0.0329, wR2 = 0.0855 |
| R indices (all data) | R1 = 0.0367, wR2 = 0.0881 |
| Largest diff. peak and hole | 0.769 and −0.474 e.Å$^{-3}$ |

TABLE 2

Atomic coordinates (×10$^4$) and equivalent isotropic displacement parameters (Å$^2$ × 10$^3$) for SL001. U(eq) is defined as one third of the trace of the orthogonalized U$^{ij}$ tensor.

| | x | y | z | U(eq) |
|---|---|---|---|---|
| Co(1) | 2594(1) | 8240(1) | 9030(1) | 10(1) |
| N(1) | 2649(1) | 9479(1) | 7733(1) | 12(1) |
| N(2) | 2537(1) | 9031(1) | 9737(1) | 12(1) |
| N(3) | 2537(1) | 7003(1) | 10326(1) | 13(1) |
| N(4) | 2634(1) | 7450(1) | 8331(1) | 12(1) |
| C(1) | 3032(1) | 8706(1) | 6572(1) | 13(1) |
| C(2) | 2893(1) | 9530(1) | 6780(1) | 13(1) |
| C(3) | 2864(1) | 10584(1) | 6018(1) | 18(1) |
| C(4) | 2560(1) | 11174(1) | 6517(1) | 18(1) |
| C(5) | 2447(1) | 10479(1) | 7584(1) | 14(1) |
| C(6) | 2237(1) | 10783(1) | 8346(1) | 13(1) |
| C(7) | 2321(1) | 10088(1) | 9356(1) | 13(1) |
| C(8) | 2300(1) | 10368(1) | 10132(1) | 15(1) |
| C(9) | 2559(1) | 9473(1) | 10968(1) | 15(1) |
| C(10) | 2689(1) | 8643(1) | 10723(1) | 13(1) |
| C(11) | 2854(1) | 7602(1) | 11410(1) | 14(1) |
| C(12) | 2722(1) | 6848(1) | 11230(1) | 15(1) |
| C(13) | 2645(1) | 5823(1) | 12006(1) | 20(1) |
| C(14) | 2382(1) | 5369(1) | 11570(1) | 19(1) |
| C(15) | 2343(1) | 6097(1) | 10518(1) | 14(1) |
| C(16) | 2217(1) | 5875(1) | 9788(1) | 13(1) |
| C(17) | 2392(1) | 6509(1) | 8753(1) | 13(1) |
| C(18) | 2440(1) | 6224(1) | 7974(1) | 17(1) |
| C(19) | 2753(1) | 6976(1) | 7085(1) | 16(1) |
| C(20) | 2848(1) | 7751(1) | 7307(1) | 13(1) |
| C(21) | 3275(1) | 8872(1) | 5499(1) | 13(1) |
| C(22) | 2545(1) | 9176(1) | 4912(1) | 16(1) |
| C(23) | 2763(1) | 9248(1) | 3948(1) | 16(1) |
| C(24) | 3727(1) | 9027(1) | 3542(1) | 16(1) |
| C(25) | 4473(1) | 8737(1) | 4096(1) | 20(1) |
| C(26) | 4237(1) | 8669(1) | 5064(1) | 18(1) |
| C(27) | 1973(1) | 11913(1) | 8054(1) | 14(1) |
| C(28) | 1049(1) | 12506(1) | 7787(1) | 17(1) |
| C(29) | 765(1) | 13549(1) | 7544(1) | 20(1) |
| C(30) | 1421(1) | 14024(1) | 7558(1) | 20(1) |
| C(31) | 2351(1) | 13462(1) | 7806(1) | 18(1) |
| C(32) | 2620(1) | 12421(1) | 8044(1) | 15(1) |
| C(33) | 2436(1) | 7291(1) | 13233(1) | 18(1) |
| C(34) | 2704(1) | 6967(1) | 14167(1) | 21(1) |
| C(35) | 3681(1) | 6612(1) | 14296(1) | 21(1) |
| C(36) | 4391(1) | 6576(1) | 13500(1) | 23(1) |
| C(37) | 4108(1) | 6909(1) | 12570(1) | 20(1) |
| C(38) | 3128(1) | 7274(1) | 12415(1) | 14(1) |
| C(39) | 1015(1) | 4737(1) | 10636(1) | 15(1) |
| C(40) | 711(1) | 3852(1) | 10914(1) | 17(1) |
| C(41) | 1353(1) | 3079(1) | 10683(1) | 18(1) |
| C(42) | 2291(1) | 3185(1) | 10206(1) | 16(1) |
| C(43) | 2581(1) | 4073(1) | 9946(1) | 15(1) |
| C(44) | 1944(1) | 4885(1) | 10130(1) | 14(1) |
| F(1) | 1602(1) | 9393(1) | 5284(1) | 30(1) |
| F(2) | 2044(1) | 9522(1) | 3407(1) | 27(1) |

TABLE 2-continued

Atomic coordinates (×10$^4$) and equivalent isotropic displacement parameters (Å$^2$ × 10$^3$) for SL001. U(eq) is defined as one third of the trace of the orthogonalized U$^{ij}$ tensor.

| | x | y | z | U(eq) |
|---|---|---|---|---|
| F(3) | 3939(1) | 9082(1) | 2615(1) | 24(1) |
| F(4) | 5403(1) | 8511(1) | 3702(1) | 41(1) |
| F(5) | 4971(1) | 8376(1) | 5589(1) | 34(1) |
| F(6) | 398(1) | 12067(1) | 7761(1) | 23(1) |
| F(7) | −125(1) | 14097(1) | 7285(1) | 31(1) |
| F(8) | 1172(1) | 15034(1) | 7302(1) | 30(1) |
| F(9) | 2984(1) | 13935(1) | 7803(1) | 25(1) |
| F(10) | 3528(1) | 11903(1) | 8268(1) | 21(1) |
| F(11) | 1482(1) | 7618(1) | 13134(1) | 31(1) |
| F(12) | 2024(1) | 6986(1) | 14948(1) | 35(1) |
| F(13) | 3946(1) | 6290(1) | 15197(1) | 31(1) |
| F(14) | 5335(1) | 6232(1) | 13636(1) | 43(1) |
| F(15) | 4807(1) | 6870(1) | 11812(1) | 36(1) |
| F(16) | 362(1) | 5490(1) | 10838(1) | 20(1) |
| F(17) | −206(1) | 3766(1) | 11358(1) | 24(1) |
| F(18) | 1063(1) | 2238(1) | 10905(1) | 25(1) |
| F(19) | 2915(1) | 2433(1) | 9994(1) | 22(1) |
| F(20) | 3503(1) | 4136(1) | 9505(1) | 20(1) |
| Cl(1) | −2992(1) | 8176(1) | 7157(1) | 19(1) |
| O(1A) | −3011(1) | 8602(1) | 7822(1) | 26(1) |
| O(2A) | −2962(1) | 7084(1) | 7750(1) | 35(1) |
| O(3A) | −2148(1) | 8352(1) | 6399(1) | 37(1) |
| O(4A) | −3858(1) | 8677(1) | 6665(1) | 33(1) |
| C(1A) | 8024(1) | 6352(1) | 5777(1) | 27(1) |
| C(2A) | 8638(1) | 5692(1) | 5377(1) | 31(1) |
| C(3A) | 8248(1) | 5301(1) | 4944(1) | 33(1) |
| C(4A) | 7248(1) | 5579(1) | 4901(1) | 32(1) |
| C(5A) | 6634(1) | 6231(1) | 5311(1) | 31(1) |
| C(6A) | 7023(1) | 6618(1) | 5751(1) | 28(1) |
| O(1B) | 1192(1) | 8648(1) | 9099(1) | 18(1) |
| C(1B) | 516(1) | 8381(2) | 10001(1) | 27(1) |
| C(1C) | 466(6) | 8937(11) | 9760(8) | 27(1) |
| O(2B) | 485(1) | 9122(1) | 7550(1) | 27(1) |
| C(2B) | 194(1) | 10210(1) | 6980(1) | 35(1) |
| O(3B) | −361(1) | 8309(1) | 6850(1) | 33(1) |
| C(3B) | 167(1) | 7767(1) | 6269(1) | 35(1) |
| O(4B) | 3986(1) | 7871(1) | 8962(1) | 19(1) |
| C(4C) | 4555(4) | 8675(5) | 8636(6) | 35(2) |
| C(4D) | 4666(4) | 6996(5) | 8870(9) | 63(3) |
| O(5B) | 4917(1) | 9244(1) | 8515(1) | 36(1) |
| C(5B) | 4999(1) | 9359(2) | 9359(2) | 32(1) |
| O(6B) | 5050(7) | 6648(6) | 8153(6) | 38(1) |
| C(6B) | 5075(3) | 5599(3) | 8957(6) | 57(2) |
| O(6C) | 5181(8) | 6480(9) | 8462(9) | 49(2) |
| C(6C) | 5030(4) | 5856(5) | 8104(6) | 47(2) |

Device Characterization

Devices were fabricated by drop-casting a suspension of SWCNTs and the desired porphyrin complex between gold electrodes (1 mm gap) in a 14-channel array with a shared counter-electrode, a design for simultaneous measurement with different composites. See, for example, J. M. Schnorr, et al., *Adv. Funct. Mater.* 2013, 23, 5285-5291, which is incorporated by reference in its entirety. The responses to various concentrations of $NH_3$ can be calibrated. Low concentrations of $NH_3$ diluted in $N_2$ were delivered to the device while a potentiostat applied 0.100 V across the electrodes and recorded current. Negative change in current resulting from exposure to $NH_3$ was divided by initial current to give change in conductance ($-\Delta G/G_0$), which was taken as the response.

Figure 2A:
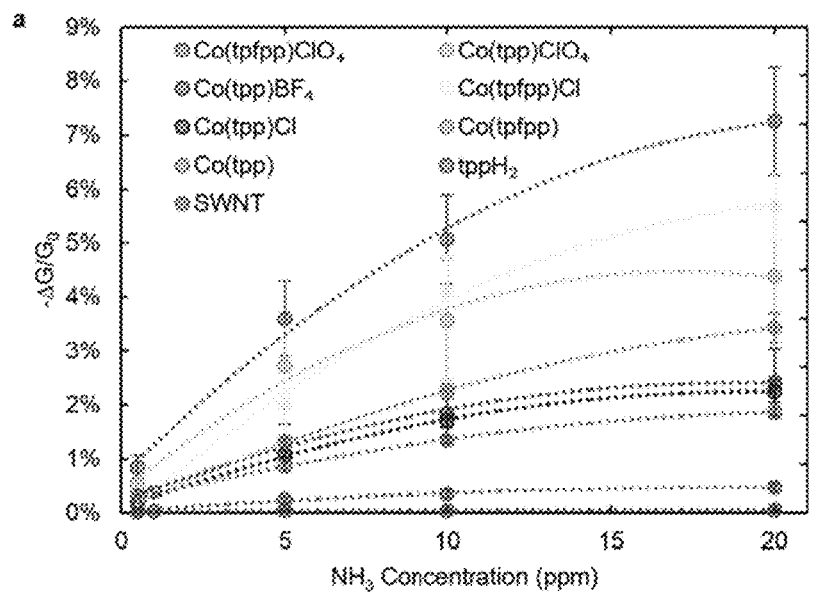
FIG. 2A shows conductance changes of detectors fabricated from porphyrin-SWCNT composites in response to 30 second exposures of various concentrations of $NH_3$ in $N_2$ (quadratic fit)
Figure 2B:
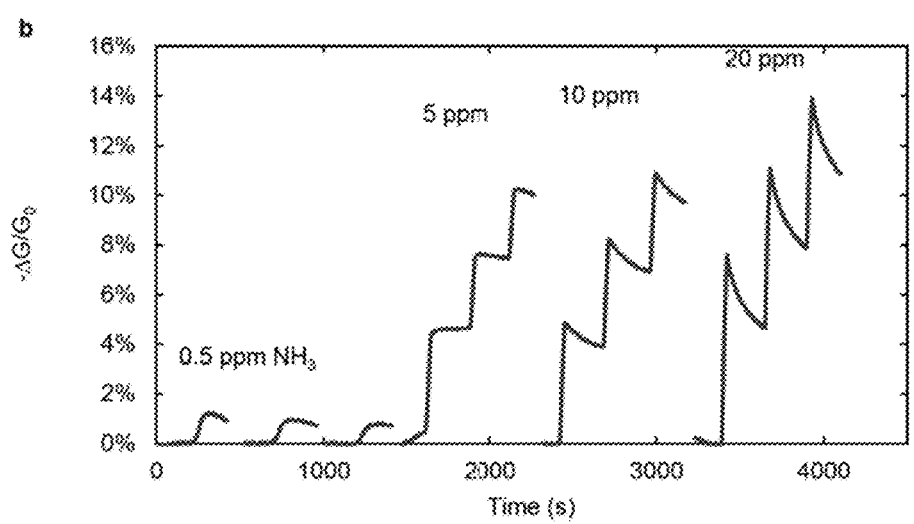
FIG. 2B shows conductance traces of a $[Co(tpfpp)]ClO_4$-SWCNT chemiresistor to three 30 second exposures of various concentrations of $NH_3$ in $N_2$.

FIG. 2A shows the average responses for two devices of each of the materials to three 30 s exposures to $NH_3$. The responses are approximately linear below 10 ppm, at which they appear to saturate. The responses change from irreversible to semi-reversible around this concentration as seen in FIG. 2B, which shows the baseline-corrected conductance traces of a [Co(tpfpp)]ClO$_4$-based device responding to NH$_3$. The device can detect less than 0.5 ppm NH$_3$. Their sensitivity toward NH$_3$ is more than an order of magnitude greater than that of pristine SWCNTs.

Figure 3:
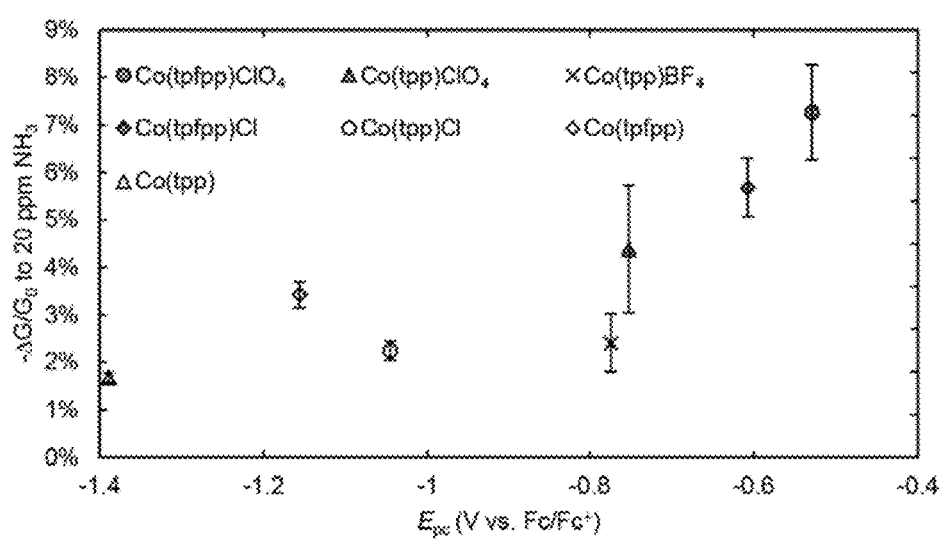
FIG. 3 shows responses of detectors fabricated from SWCNT/Co-porphyrin composites to 30 second exposures of 20 ppm $NH_3$ against reduction potentials (potential of first peak cathodic current as measured by cyclic voltammetry of the compounds in PhCN solution vs. $Fc/Fc^+$).

Sensitivity to amines can improve with increased electron deficiency at the Co center. Using the first reduction potential of the complexes as a proxy for electron deficiency, the correlation between sensitivity to NH$_3$ and electron deficiency at the Co center can be investigated. FIG. 3 shows the response of the Co composites to 20 ppm NH$_3$ against the first reduction potential of the Co complex. These results suggest that efficacy for NH$_3$ detection in this system improves with increasing electron deficiency at the metal center.

Figure 4A:
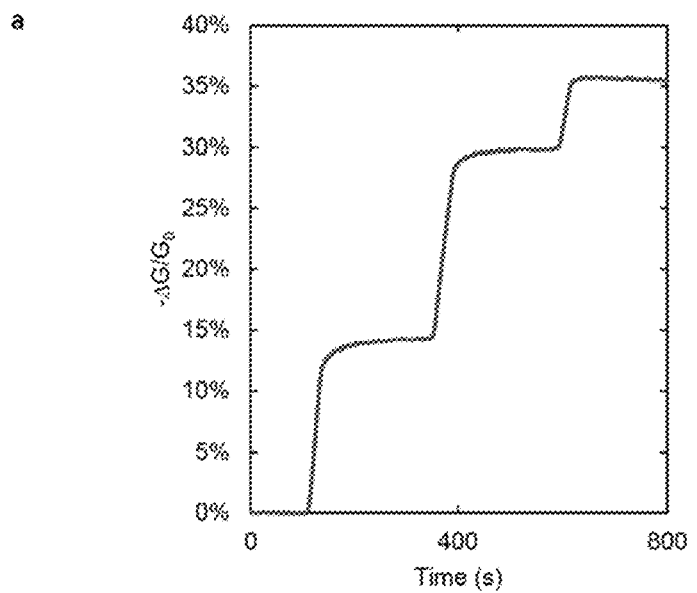
FIGS. 4A-4B shows conductance traces of a $[Co(tpfpp)]ClO_4$-SWCNT chemiresistor to three 30 second exposures of 2.5 ppm of a) putrescine (FIG. 4A) and b) cadaverine (FIG. 4B).
Figure 4B:
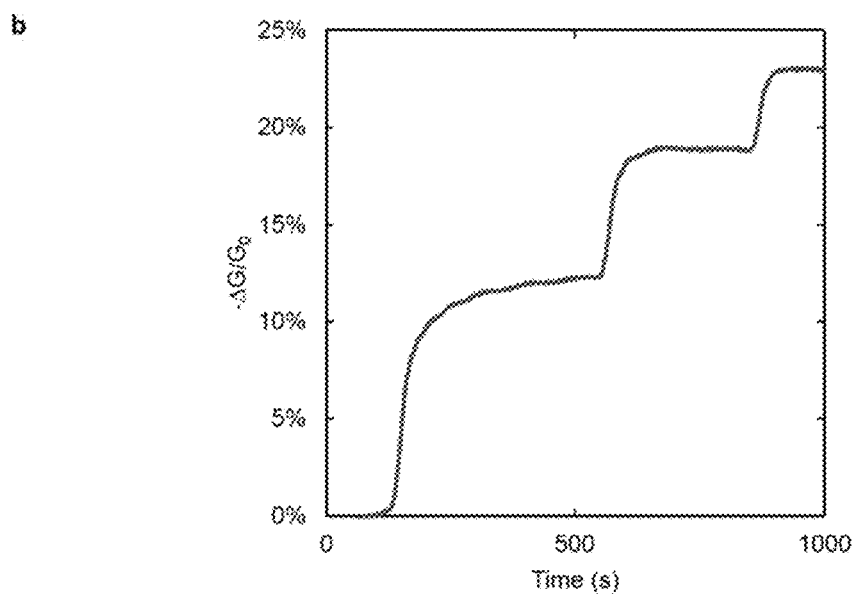

For monitoring meat spoilage, the detection of BAs such as putrescine and cadaverine is pertinent. FIG. 4 shows the responses of [Co(tpfpp)]ClO$_4$-SWCNT chemiresistors to exposures of both putrescine (FIG. 4A) and cadaverine (FIG. 4B). The strong responses are dosimetric and can find utility in single-use wireless tags. See, for example, J. M. Azzarelli, et al., Proc. Natl. Acad. Sci. USA 2014, 111, 18162-18166, which is incorporated by reference in its entirety.

Figure 5:
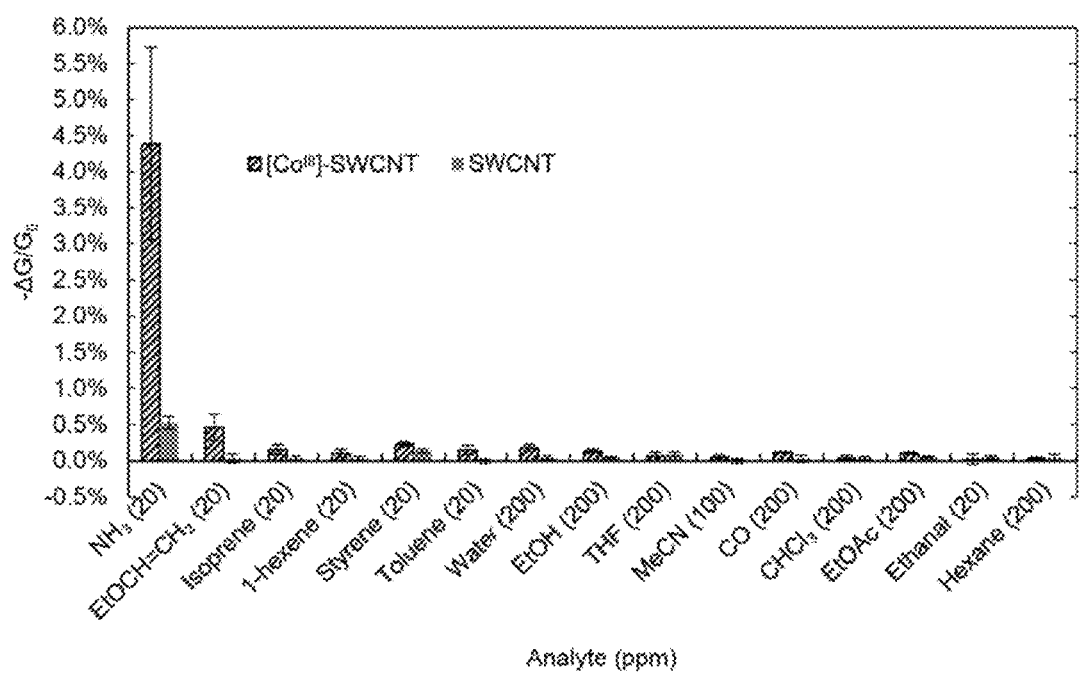
FIG. 5 shows responses of $[Co(tpp)]ClO_4$-SWCNT and non-functionalized SWCNT chemiresistors to 30 second exposures of various compounds' vapors (concentration) in $N_2$.

Detection of BAs in meat samples requires a strategy for distinguishing them from the complex matrix. To assess their selectivity toward amines, responses of [Co(tpp)]ClO$_4$-SWCNT devices to volatile compounds representing a wide range of functional groups can be measured (FIG. 5). The devices exhibit high selectivity for NH$_3$ among the analytes tested. Species capable of simply coordinating to the Co$^{3+}$ center (e.g., H$_2$O, EtOH, THF, CO) do not elicit a strong response, suggesting that charge transfer is a large component of signal transduction for amines in this system. While the devices alone cannot distinguish amines from each other, their response will reflect the TVBN level with minor contribution from interferents.

Figure 6A:
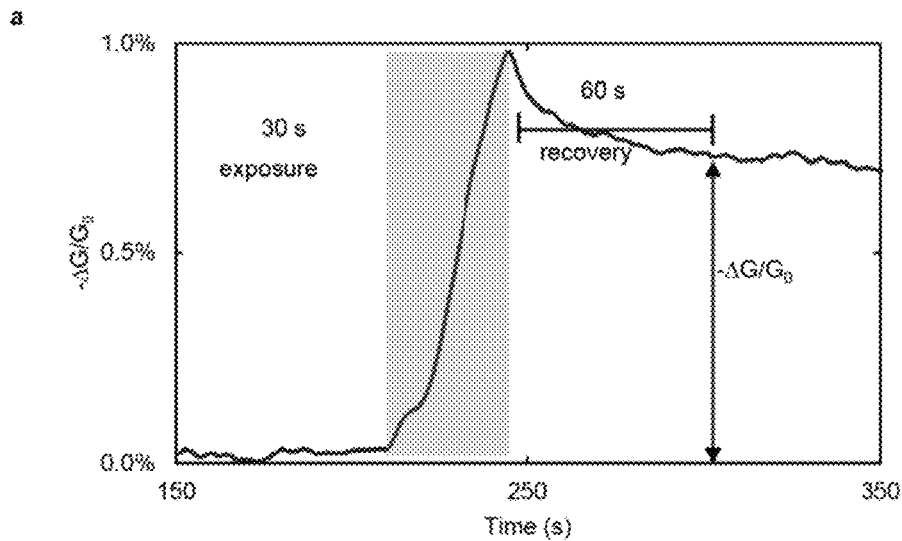
FIG. 6A shows conductance trace of $[Co(tpp)]ClO_4$-SWCNT chemiresistor during 30 s exposure to vapors from 1.0 g pork after storage at 22° C. for 4 days.

The detector can be used to compare TVBN emission from day to day for 1.0 g aliquots of various types of raw meat: pork, chicken, salmon, and cod. A sample was placed in a gas flow chamber. See, for example, B. Esser, et al., Angew. Chem. 2012, 124, 5851-5855; B. Esser, et al., Angew. Chem. Int. Ed. 2012, 51, 5752-5756, each of which is incorporated by reference in its entirety. N$_2$ (0.25 L/min) was passed alternately over the detector or first through the chamber holding the meat sample at 25° C. before passing over the detector. The initial peak response at the end of a 30 s exposure was not as reproducible as the ΔG values taken 60 s after the end of the exposure (FIG. 6A). This effect may be the result of unknown interfering analytes that give a reversible sensor response. As shown in FIG. 4, target BAs are likely to give irreversible responses over time periods reflected in this scheme. Hence, the delay gives a more faithful measurement of these key BAs.

Figure 6B:
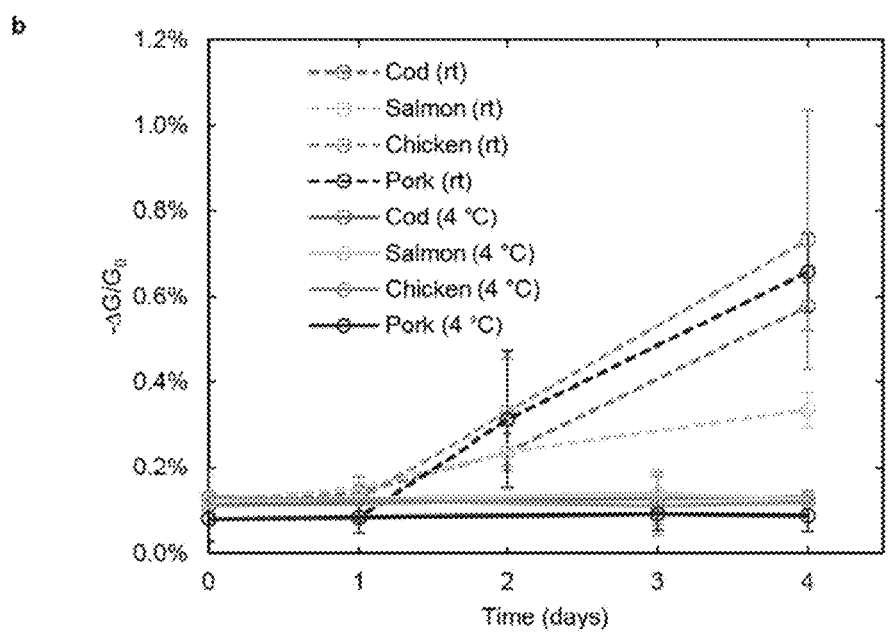
FIG. 6B shows responses of device to 30 second exposures of vapors from various 1.0 g meat samples stored at 22° C. (rt) or 4° C. for 0-4 days.
Figure 7:
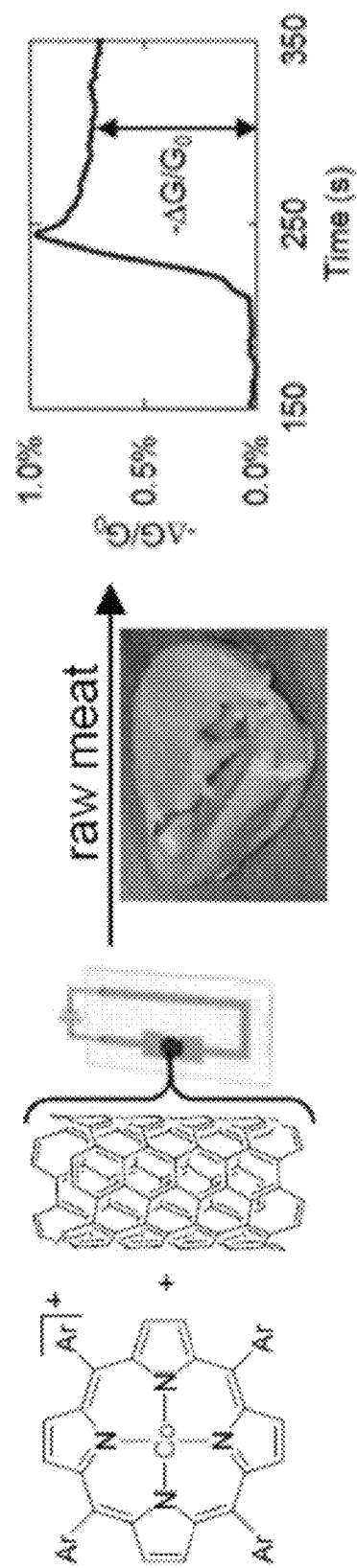
FIG. 7 shows the detection of meat spoilage.
Figure 8:
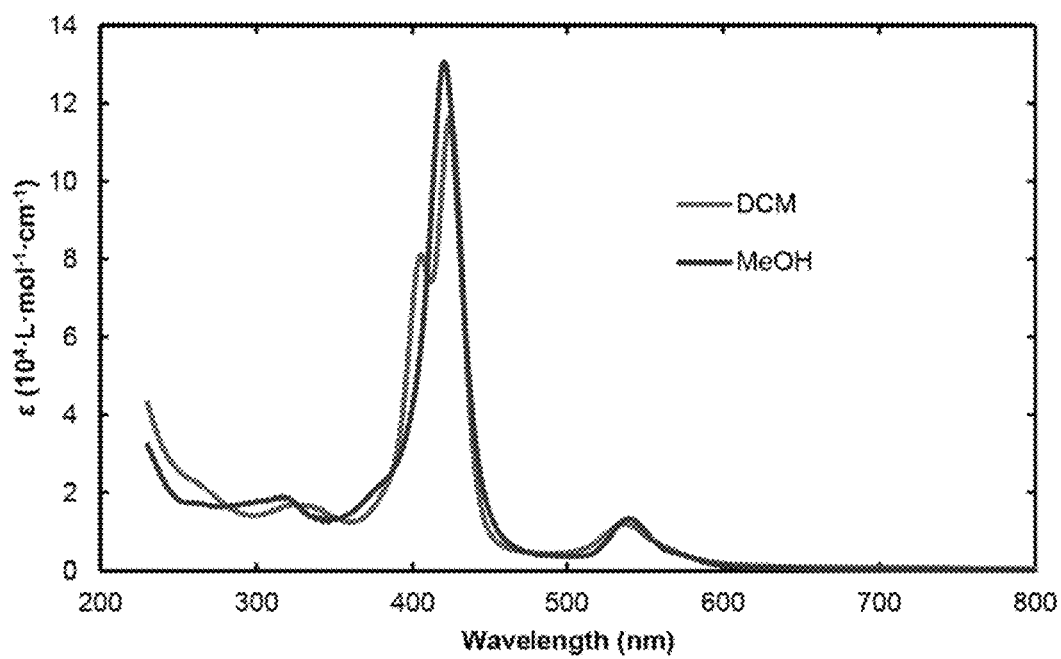
FIG. 8 shows UV-Vis spectrum of [Co(tpfpp)]ClO$_4$ in dichloromethane (DCM) and in methanol (MeOH).
Figure 9:
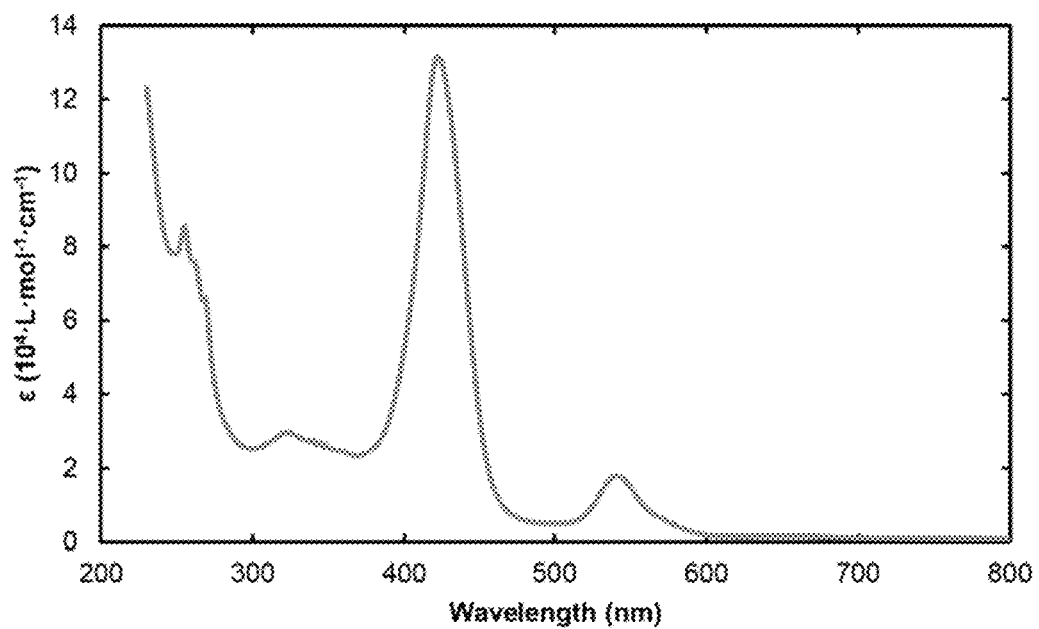
FIG. 9 shows UV-Vis spectrum of [Co(tpfpp)Cl] in dichloromethane.
Figure 10:
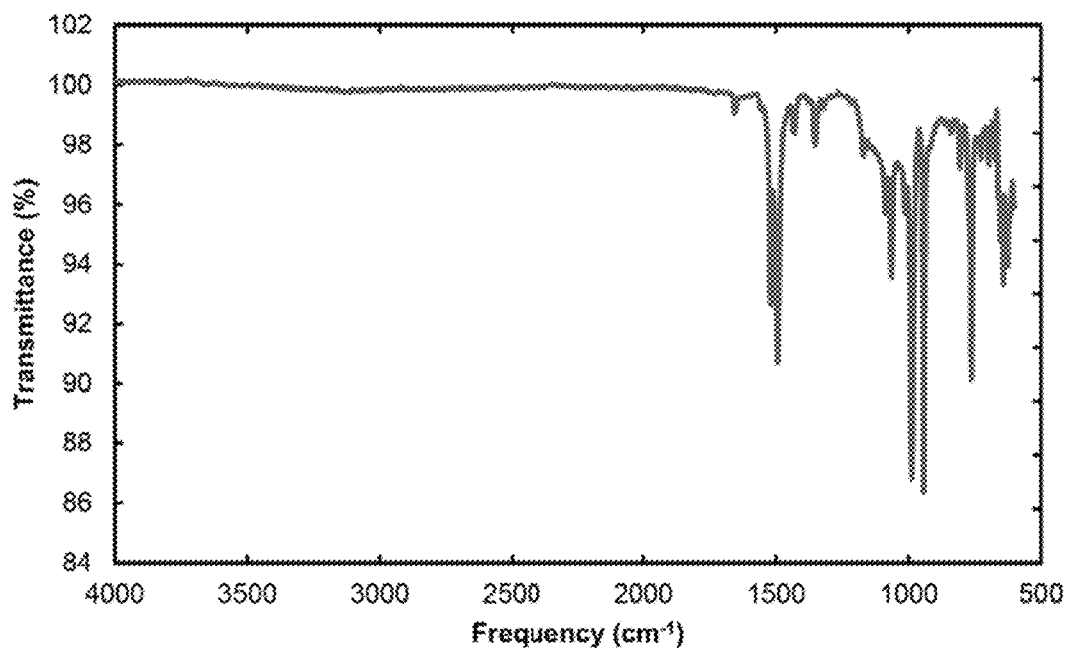
FIG. 10 shows IR spectrum of [Co(tpfpp)(H$_2$O)$_2$]ClO$_4$.
Figure 11:
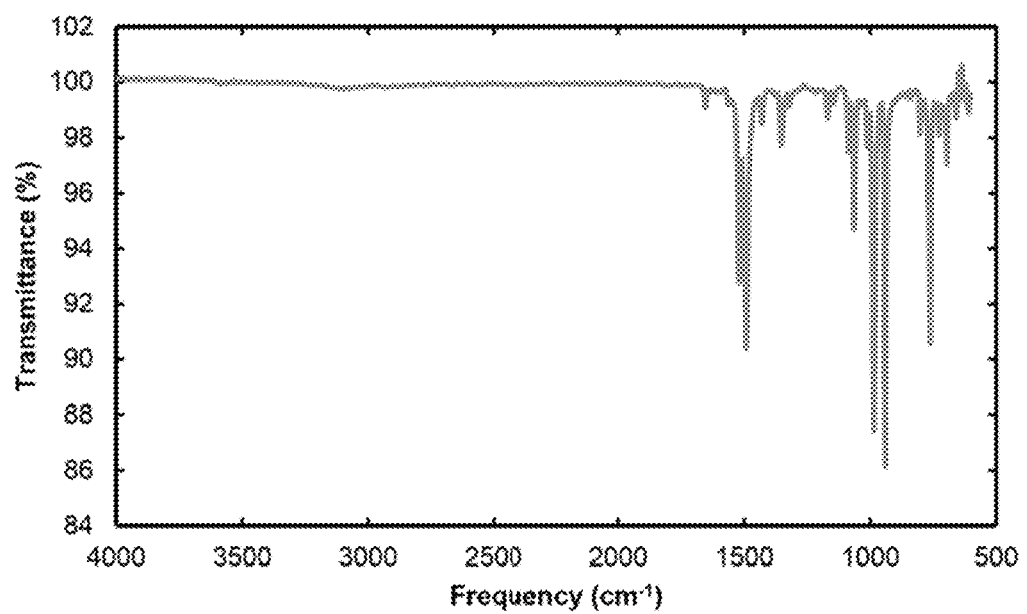
FIG. 11 shows IR spectrum of [Co(tpfpp)(H$_2$O)Cl].
Figure 12:
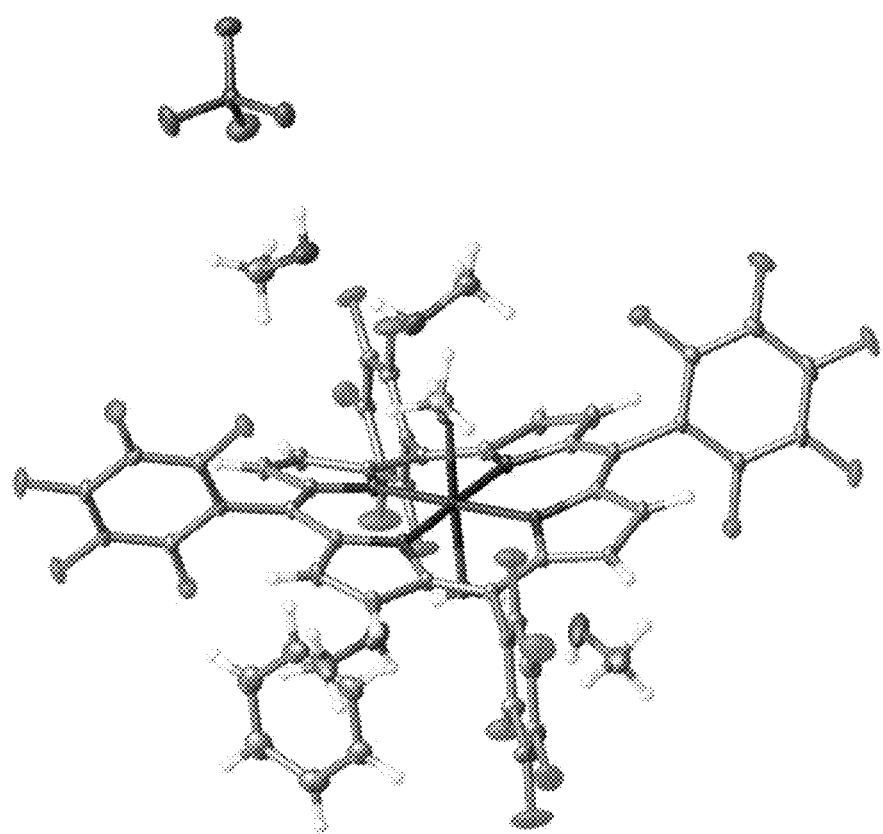
FIG. 12 shows thermal ellipsoid depiction of [(tpfpp)Co(ClO$_4$)]. Only the largest components of solvent disorder are shown.
Figure 13:
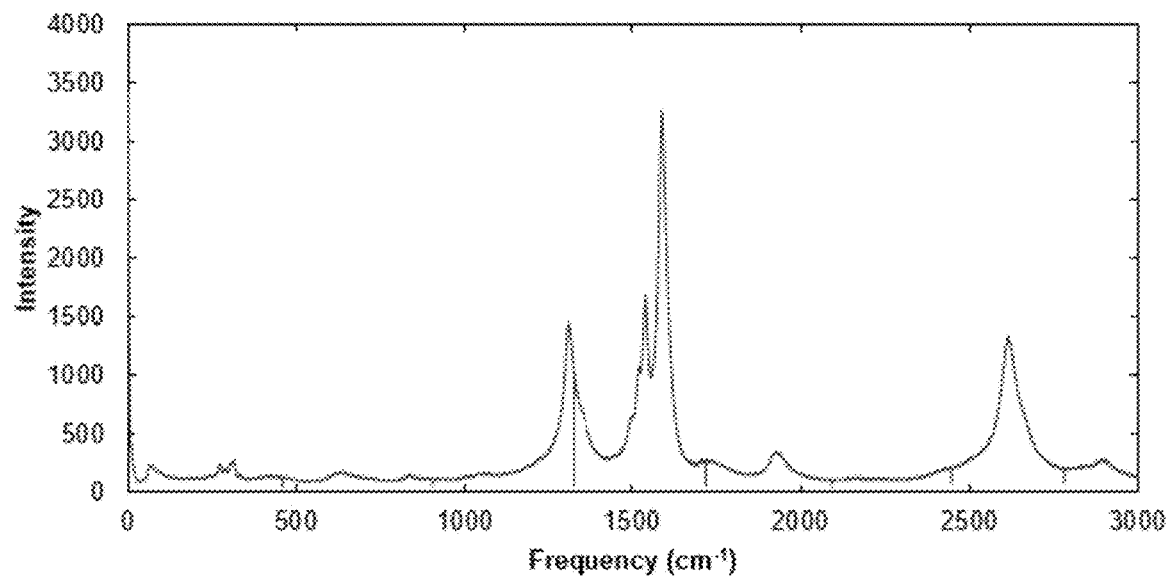
FIG. 13 shows Raman spectrum of [Co(tpp)]ClO$_4$-SWCNT composite (633 mm excitation).
Figure 14:
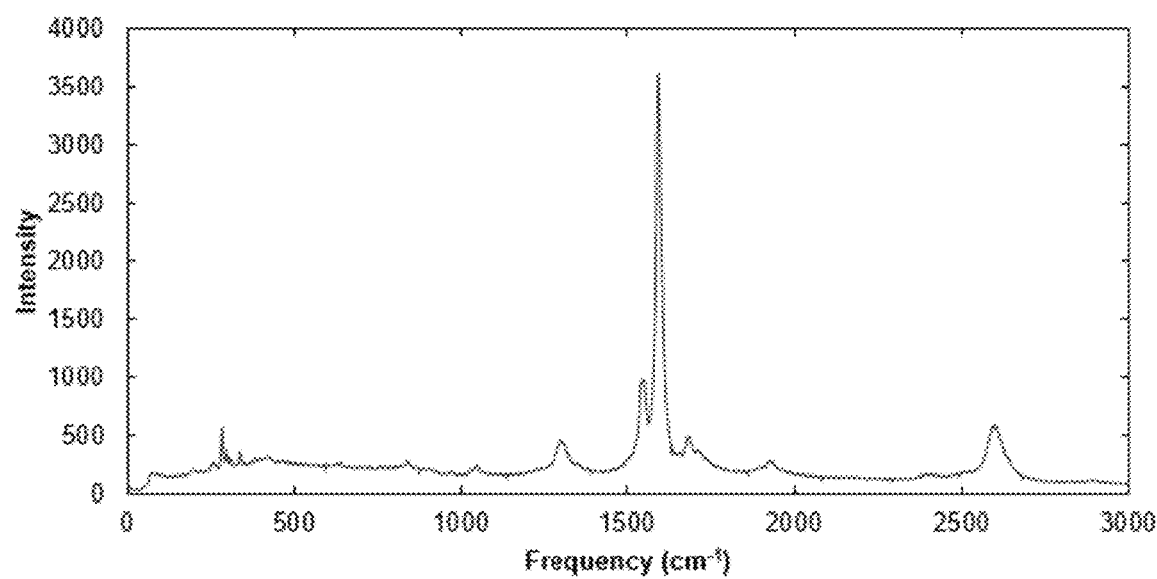
FIG. 14 shows Raman spectrum of tppH$_2$-SWCNT composite (633 mm excitation).
Figure 15:
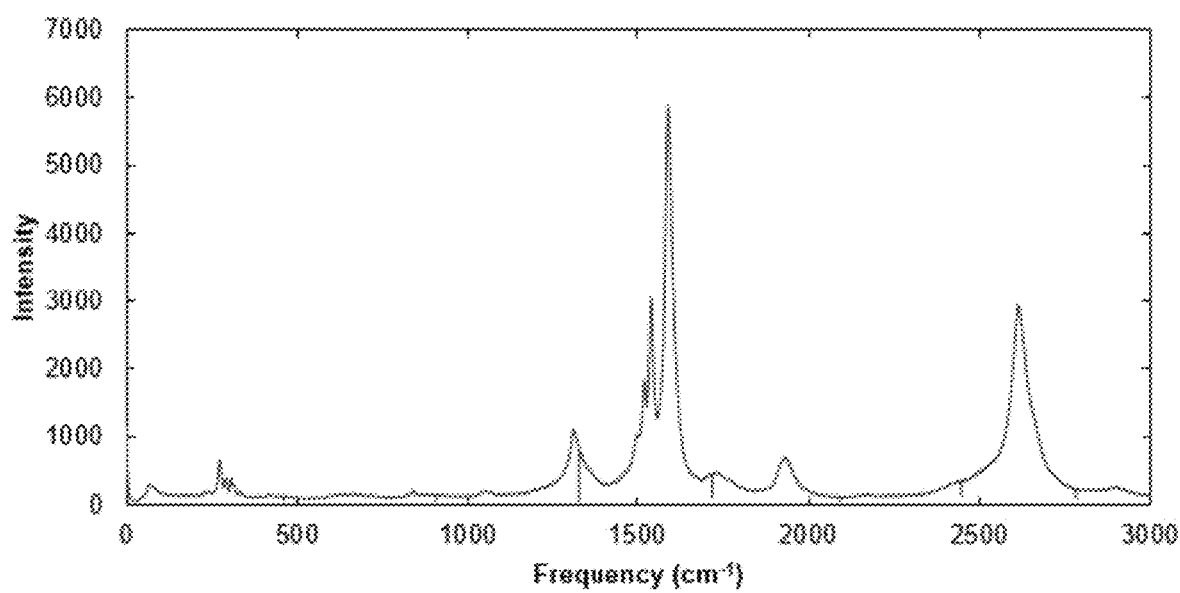
FIG. 15 shows Raman spectrum of SWCNTs (633 mm excitation).

The results of the meat monitoring measurements made with the same [Co(tpp)]ClO$_4$-based device across 4 days are shown in FIG. 6B. Two samples for each meat were monitored, one stored at room temperature (22° C.) and one at 4° C. For samples stored at 4° C., the detector showed no increase in response over 4 days. The absence of observable spoilage for meat samples stored for 4 days at 4° C. is consistent with the literature. For samples stored at 22° C., an increase in response was observed after day 1, and even greater responses were recorded by day 4; this increase in TVBN content between days 1 and 2 and further increase after day 2 is consistent with literature reports for BA levels in meat determined using other techniques (electrochemistry, chromatography, and spectrometry). See, for example, G. C. Chemnitius, et al., Sens. Actuators, B 1996, 32, 107-113, which is incorporated by reference in its entirety.

Chemiresistive detectors for amines can be created from single-walled carbon nanotubes by non-covalent modification with cobalt meso-arylporphyrins. With changes in oxidation state, electron-withdrawing character of the porphyrin ligand, and counteranion, the response to ammonia can be improved. The devices can have sub-ppm sensitivity and high selectivity toward amines. The detectors can be used in monitoring meat spoilage.

Gas Detection Measurements

Gas detection measurements were acquired by using a test clip fitted with a PTFE spacer to connect the gold electrodes of the device to a PalmSens EmStat potentiostat with a MUX16 multiplexer. For ammonia detection measurements, the chemiresistive device was enclosed in a PTFE chamber, and a gas mixer system was used to deliver to the chamber low concentrations of ammonia gas diluted by nitrogen. The gas mixer was comprised of two digital mass flow controllers purchased from Sierra Instruments. A MicroTrak Mass Flow Controller is used to deliver up to 4 mL/min of a mixture of 1% ammonia in nitrogen that was further diluted in the gas mixer by nitrogen delivered by the other MFC at 2.00 L/min. The potentiostat was used to apply a constant potential of 0.100 V across the electrodes, and the current was recorded using PSTrace software (v. 3.0) as the device was exposed to varying concentrations of ammonia for 30 s at a time with at least 70 s between successive measurements. Carbon monoxide measurements were made in a similar manner, using CO in the place of the 1% NH$_3$ in nitrogen.

For measuring device response to volatile liquid organic compounds and to water, a KIN-TEK gas generator system was used after calibration for each compound. Data for amine detection measurements were corrected to a linear fit of the baseline current that was measured prior to gas exposures; for other analytes, the data were corrected to a linear fit of the baseline across the entire data acquisition time.

Figure 16A:
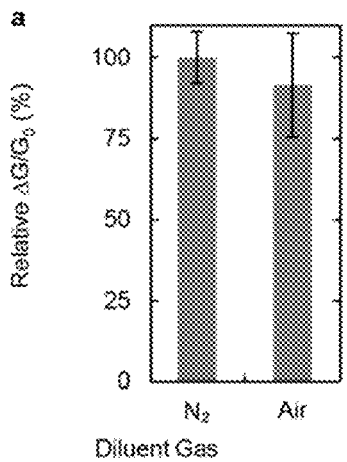
FIG. 16A shows average responses of [Co(tpp)]ClO$_4$-SWCNT devices to 1 ppm NH$_3$ in air relative to those in nitrogen.
Figure 16B:
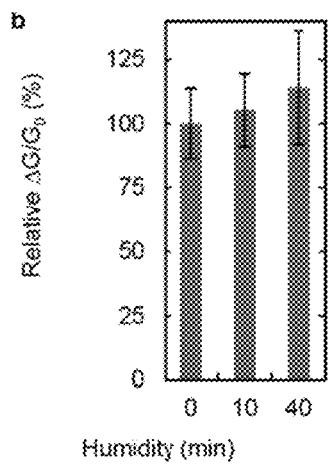
FIG. 16B shows responses of [Co(tpp)]ClO$_4$-SWCNT devices to 1 ppm NH$_3$ after 0, 10, and 40 minute exposures to air saturated with water relative to their dry responses.
Figure 16C:
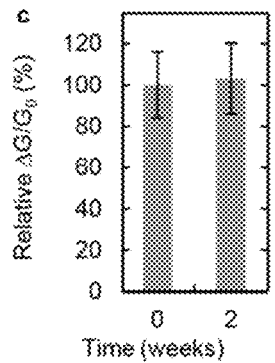
FIG. 16C shows responses of [Co(tpp)]ClO$_4$-SWCNT devices to 1 ppm NH$_3$ relative to their responses 2 weeks prior.
Figure 17:
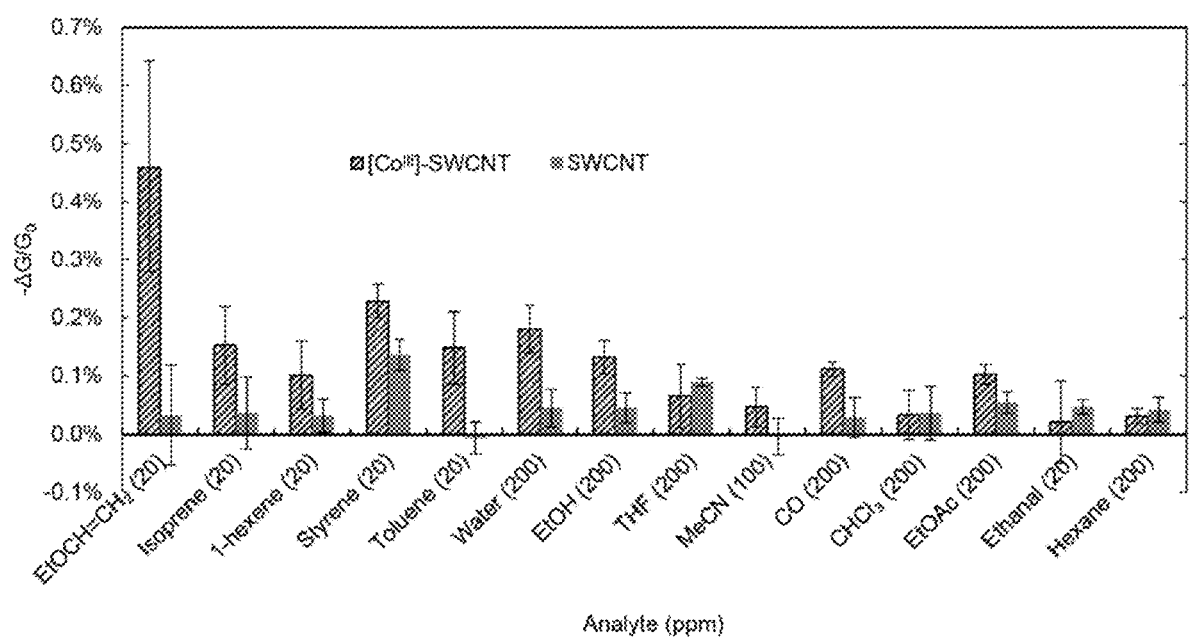
FIG. 17 shows responses of [Co(tpp)]ClO$_4$-SWCNT and non-functionalized SWCNT chemiresistors to 30 second exposures of various compounds' vapors (concentration) in N$_2$.
Figure 18:
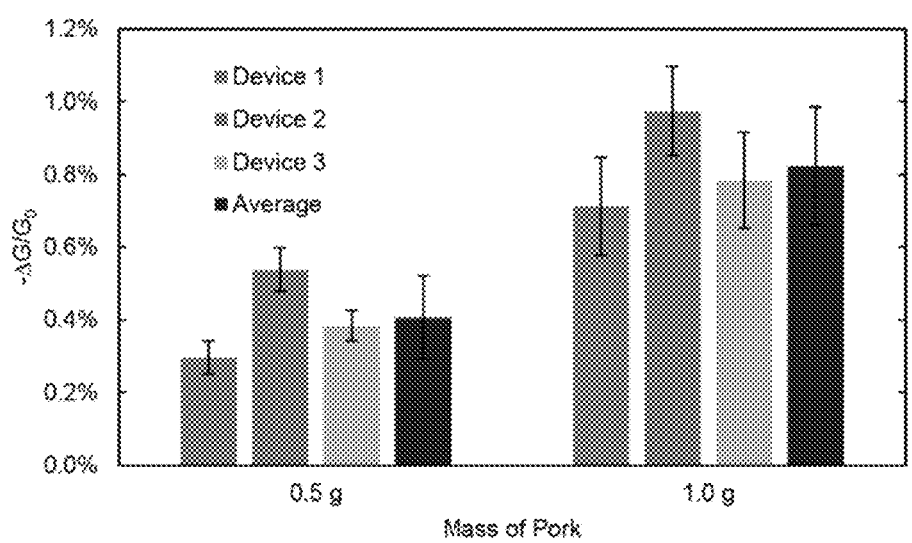
FIG. 18 shows average responses of three [Co(tpp)]ClO$_4$-SWCNT chemiresistors to three 30 second exposures of vapors from 0.5 g and 1.0 g masses of spoiled pork samples.
Figure 19:
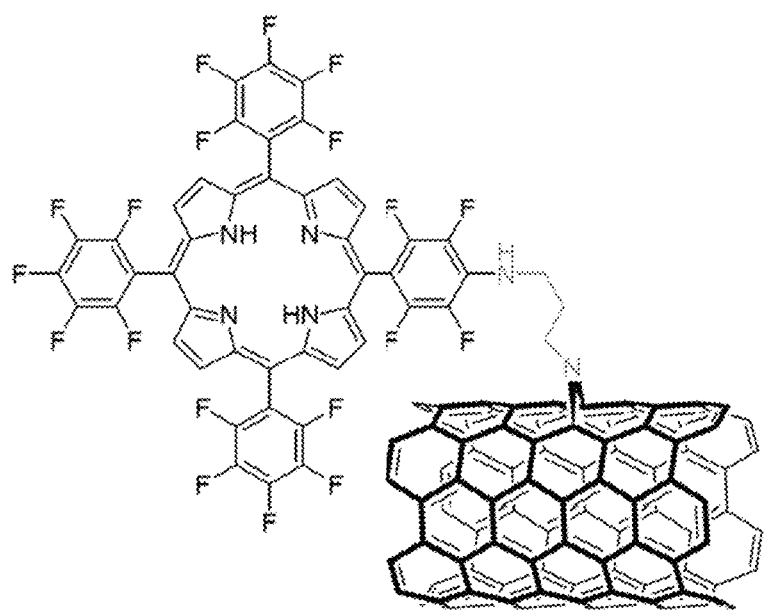
FIG. 19 shows an example structure of carbon nanotube functionalization.

As their parent Co complexes are air-stable, the devices fabricated from them can be stable to oxidation by molecular oxygen in ambient conditions. Using representative [Co(tpp)]ClO$_4^-$ based devices, to assess their stability toward oxygen, NH$_3$ detection measurements using air as the carrier gas were performed and compared to measurements made with the same devices using nitrogen as the carrier gas. As shown in FIG. 16A, the responses to NH$_3$ are negligibly affected by performing the measurements in the presence of oxygen. Likewise, as the Co porphyrin complexes are synthesized and used as their aquo adducts, device performance can be unaffected by exposure to water. Devices fabricated from [Co(tpp)]ClO$_4$ were placed in water-saturated air at 30° C. (4 kPa H$_2$O) for 10 and 40 min and then tested for their response to NH$_3$. FIG. 16B shows that this exposure to moisture did not negatively affect the device performance. FIG. 16C shows that storage under ambient conditions for two weeks also does not negatively affect device performance. FIG. 18 shows that halving the mass of the meat will also halve the detector's response, demonstrating that this experimental setup is dependent on the mass of the meat sample and not at saturation.

Other embodiments are within the scope of the following claims.

What is claimed is:

1. A sensor comprising:
   a conductive region in electrical communication with at least two electrodes, the conductive region including a complex, wherein the complex includes pristine single-walled carbon nanotubes that are functionalized by a porphyrin, wherein the porphyrin includes a sterically protected electron-deficient metal center and arranged to detect less than 0.5 ppm $NH_3$ due to proximity the electrophilicity of the metal center toward amines arranged to be enhanced through both a fluorinated porphyrin ligand and a coordinating counter anion.

2. The sensor of claim 1, wherein the porphyrin includes a cobalt porphyrin.

3. The sensor of claim 1, wherein the cobalt porphyrin includes a $Co^{3+}$.

4. The sensor of claim 1, wherein the cobalt porphyrin includes a $Co^{2+}$.

5. The sensor of claim 1, wherein the carbon nanotubes are non-covalently functionalized by the porphyrin.

6. The sensor of claim 1, wherein the carbon nanotubes are covalently functionalized.

7. The sensor of claim 1, wherein the complex includes a cobalt meso-arylporphyrin complex.

8. The sensor of claim 1, wherein the complex includes a meso-tetrakis(pentafluorophenyl)porphyrinato.

9. The sensor of claim 1, wherein the complex includes a meso-tetraphenylporphyrinato.

10. The sensor of claim 1, wherein the complex includes a meso-arylporphyrin.

11. The sensor of claim 1, wherein the porphyrin includes a $ClO_4^-$.

12. The sensor of claim 1, wherein the porphyrin includes a $BF_4^-$.

13. The sensor of claim 1, wherein the porphyrin includes a $Cl^-$.

14. A food packaging comprising a sensor, wherein the sensor includes a conductive region in electrical communication with at least two electrodes, the conductive region including a complex, wherein the complex includes pristine single-walled carbon nanotubes that are functionalized by a porphyrin, wherein the porphyrin includes a sterically protected electron-deficient metal center and arranged to detect less than 0.5 ppm $NH_3$ due to proximity the electrophilicity of the metal center toward amines arranged to be enhanced through both a through both a fluorinated porphyrin ligand and a coordinating counter anion.

* * * * *